United States Patent
Le-Khac

(10) Patent No.: US 7,453,003 B1
(45) Date of Patent: Nov. 18, 2008

(54) DIRECT EPOXIDATION CATALYST AND PROCESS

(75) Inventor: Bi Le-Khac, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 11/897,382

(22) Filed: Aug. 29, 2007

(51) Int. Cl.
*C07D 301/06* (2006.01)

(52) U.S. Cl. .......................... 549/533; 502/63; 502/64; 502/168; 502/223; 502/330

(58) Field of Classification Search ................. 549/533, 549/534; 502/63, 76, 74, 64, 168, 223, 330
See application file for complete search history.

(56) References Cited

U.S. PATENT DOCUMENTS

| | | | | |
|---|---|---|---|---|
| 4,410,501 | A | 10/1983 | Taramasso et al. | 423/326 |
| 4,701,423 | A | 10/1987 | Bellussi et al. | 502/8 |
| 4,833,260 | A | 5/1989 | Neri et al. | 549/531 |
| 4,954,325 | A | 9/1990 | Rubin et al. | 423/328 |
| 4,954,653 | A | 9/1990 | Bellussi et al. | 564/223 |
| 5,500,199 | A | 3/1996 | Bellussi et al. | 423/328.2 |
| 5,623,090 | A | 4/1997 | Haruta et al. | 568/360 |
| 5,861,536 | A * | 1/1999 | Durante et al. | 564/408 |
| 6,005,123 | A | 12/1999 | Dessau et al. | 549/531 |
| 6,008,388 | A | 12/1999 | Dessau et al. | 549/531 |
| 6,077,498 | A | 6/2000 | Diaz Cabanas et al. | 423/702 |
| 6,106,803 | A | 8/2000 | Hasenzahl et al. | 423/705 |
| 6,114,551 | A | 9/2000 | Levin et al. | 549/510 |
| 6,252,095 | B1 * | 6/2001 | Hayashi et al. | 549/523 |
| 6,362,349 | B1 | 3/2002 | Kuperman et al. | 549/533 |
| 6,498,259 | B1 | 12/2002 | Grey et al. | 549/533 |
| 6,524,984 | B2 | 2/2003 | Carati et al. | 502/64 |
| 6,646,142 | B1 | 11/2003 | Meima et al. | 549/536 |
| 6,849,570 | B2 | 2/2005 | Hasenzahl et al. | 502/242 |
| 2007/0027347 | A1 | 2/2007 | Miller et al. | 568/959 |

FOREIGN PATENT DOCUMENTS

| | | |
|---|---|---|
| BE | 1001038 A7 | 6/1989 |
| JP | 4-352771 | 12/1992 |
| WO | WO 2006/130295 | 12/2006 |

OTHER PUBLICATIONS

T. Kang et al., *Ind. Eng. Chem. Res. 43* (2004) 1478.
H. Sato et al., *J. Chem. Eng. of Japan 35 (3)* (2002) 255.
R. Szostak, "Non-aluminosilicate Molecular Sieves", In *Molecular Principles of Synthesis and Identification* (1989) 205.
G. Vayssilov, *Catal. Rev.-Sci. Eng. 38(3)* (1997) 209.
T. Maschmeyer et al., *Nature 378* (1995) 159.
P. Tavev et al., *Nature 368* (1994) 321.
A. Coma, *J. Chem.Soc., Chem. Commun.* (1998) 579.
D. Wei et al., *Catal. Today 51* (1999) 501.
K. Masters, *Spray Drying in Practice*, SprayDryConsultant International ApS. (2002) 1-15.
Y. Izumi et al., "Chapter 2 Clay as Potential Catalyst Material" in *Zeolite, Clay, and Heteropoly Acid in Organic Reactions* (1992) 49.
T. W. Healy, "Stability of Aqueous Silica Sols" in *The Colloid Chemistry of Silica* (1994) 147.

* cited by examiner

*Primary Examiner*—B. Dentz
*Assistant Examiner*—David E Gallis
(74) *Attorney, Agent, or Firm*—Yuanzhang Han

(57) ABSTRACT

A catalyst comprising a transition metal zeolite, a noble metal, and a thiol is disclosed. The catalyst is used in an epoxidation process comprising reacting an olefin, hydrogen, and oxygen. The presence of a thiol in the catalyst reduces the formation of alkanes from the hydrogenation of olefins, and/or improves hydrogen and oxygen selectivities to epoxides.

15 Claims, No Drawings

DIRECT EPOXIDATION CATALYST AND PROCESS

FIELD OF THE INVENTION

The invention relates to a catalyst comprising a transition metal zeolite, a noble metal, and a thiol. The catalyst is used to produce an epoxide by reacting an olefin, hydrogen, and oxygen.

BACKGROUND OF THE INVENTION

Direct epoxidation of higher olefins (containing three or more carbons) such as propylene with oxygen and hydrogen has been the focus of recent efforts. For example, the reaction may be performed in the presence of a catalyst comprising gold and a titanium-containing carrier (see, e.g., U.S. Pat. Nos. 5,623,090, 6,362,349, and 6,646,142), or a catalyst containing palladium and a titanium zeolite (see, e.g., JP 4-352771; U.S. Pat. Nos. 6,008,388, 6,498,259). Unfortunately, these catalyst systems also produce alkanes from the corresponding olefins. U.S. Pat. No. 6,005,123 discloses that a sulfur compound may be used to inhibit propane formation in the epoxidation of propylene, but it also inhibits the epoxides formation. There is a continued need to find new catalysts that inhibit hydrogenation of olefin without decreasing its epoxidation activity.

Thiol-functionalized mesoporous silicas are reported to selectively adsorb $Pt^{2+}$ and $Pd^{2+}$ (see *Ind. Eng. Chem. Res.* 43 (2004) 1478). On the other hand, the hydrogenation activity of Pt or Pd is strongly inhibited by the thiol functionality (see *J. Chem. Eng. of Japan* 35(3) (2002) 255).

SUMMARY OF THE INVENTION

The invention is a catalyst comprising a transition metal zeolite, a noble metal, and a thiol. The catalyst is useful in producing an epoxide from an olefin, hydrogen, and oxygen. The presence of a thiol in the catalyst reduces the formation of alkanes from hydrogenation of olefins, and/or improves hydrogen and oxygen selectivities to epoxides.

DETAILED DESCRIPTION OF THE INVENTION

In one aspect, the invention is a catalyst comprising a transition metal zeolite, a noble metal, and a thiol. Zeolites are porous crystalline solids with well-defined structures. Generally they contain one or more of Si, Ge, Al, B, P, or the like, in addition to oxygen. Many zeolites occur naturally as minerals and are extensively mined in many parts of the world. Others are synthetic and are made commercially for specific uses. Zeolites have the ability to act as catalysts for chemical reactions which take place mostly within their internal cavities. Transition metal zeolites are zeolites comprising transition metals in framework. A transition metal is a Group 3-12 element. The first row of transition metals are from Sc to Zn. Preferred transition metals are Ti, V, Mn, Fe, Co, Cr, Zr, Nb, Mo, and W. More preferred are Ti, V, Mo, and W. Most preferred is Ti.

Preferred titanium zeolites are titanium silicates (titanosilicates). Preferably, they contain no element other than titanium, silicon, and oxygen in is the lattice framework (see R. Szostak, "Non-aluminosilicate Molecular Sieves," in *Molecular Sieves: Principles of Synthesis and Identification* (1989), Van Nostrand Reinhold, pp. 205-82). Small amounts of impurities, e.g., boron, iron, aluminum, phosphorous, copper, and the like, and mixtures thereof, may be present in the lattice. The amount of impurities is preferably less than 0.5 wt. %, more preferably less than 0.1 wt. %. Preferred titanium silicates will generally have a composition corresponding to the following empirical formula: $xTiO_2 \cdot (1-x)SiO_2$, where x is between 0.0001 and 0.5000. More preferably, the value of x is from 0.01 to 0.125. The molar ratio of Si to Ti in the lattice framework of the zeolite is advantageously from 9.5:1 to 99:1, most preferably from 9.5:1 to 60:1. Particularly preferred titanium zeolites are titanium silicalites (see Catal. *Rev. Sci. Eng.*, 39(3) (1997) 209). Examples of these include TS-1 (titanium silicalite-1, a titanium silicalite having an MFI topology analogous to that of the ZSM-5 aluminosilicate), TS-2 (having an MEL topology analogous to that of the ZSM-11 aluminosilicate), and TS-3 (as described in Belgian Pat. No. 1,001,038). Titanium zeolites having framework structures isomorphous to zeolite beta, mordenite, ZSM-12, MCM-22, MCM-41, and MCM-48 are also suitable for use. Examples of MCM-22, MCM-41, and MCM-48 zeolites are described in U.S. Pat. Nos. 4,954,325, 6,077,498, and 6,114,551; Maschmeyer, T., et al, *Nature* 378(9) (1995) 159; Tanev, P. T., et al., *Nature* 368 (1994) 321; Corma, A., *J. Chem. Soc. Chem. Commun.* (1998) 579; Wei D., et al., Catal. *Today* 51 (1999) 501). The most preferred is TS-1.

Transition metal zeolites may be formed into particles. Spray drying is a preferred forming technique. Spray drying is a suspended particle processing system that utilizes liquid atomization to create droplets that are dried to individual particles while moving in a gaseous medium (see K. Maters, *Spray Drying In Practice*, SprayDryConsultant International ApS (2002) pp. 1-15). Spray drying is known in forming zeolites, including titanium zeolites (see, e.g., U.S. Pat. Nos. 4,954,653, 4,701,428, 5,500,199, 6,524,984, and 6,106,803).

A transition metal zeolite containing templating agent may be used to form particles. A transition metal zeolite is generally prepared in the presence of an organic templating agent (see, e.g., U.S. Pat. No. 6,849,570). Suitable templating agents include alkyl amines, quaternary ammonium compounds, etc. When a zeolite is crystallized, it usually contains organic templating agent within its pores, which can be removed by calcination or solvent extraction. Zeolites containing templating agents may be spray dried without being treated by calcination or solvent extraction. Alternatively, a zeolite that is free of templating agent may be spray dried.

A binder is preferably used in spray drying the transition metal zeolite. A binder helps to improve the mechanical strength or the physical properties of spray-dried particles (e.g., crushing strength, surface area, pore size, pore volume). Sometimes the binder can modify the chemical properties (e.g., acidity, basicity) of the active component (e.g., the transition metal zeolite) and its catalytic activity. Suitable binders include metal oxides, non-metal oxides, mixed oxides, clays, and the like. Examples of suitable binders include silicas, aluminas, titanias, magnesias, silica-aluminas, silica-titanias, clays, and the like, and mixtures thereof. Examples of clays can be found in "Chapter 2. Clay as Potential Catalyst Material," *Zeolite, Clay, and Heteropoly Acid in Organic Reactions* (1992) Kodansha Ltd., Tokyo. Preferred binders are silicas, aluminas, titanias, silica-aluminas, silica-titanias, and mixtures thereof. More preferred are silicas, aluminas, titanias, and mixtures thereof. Precursors of binders are often used in preparing the mixture for spray drying. For example, silica may be introduced into the mixture as a silica sol (Healy, T. W., "Stability of Aqueous Silica Sols," in *The Colloid Chemistry of Silica* (1994) American Chemical Society). Similarly, other binder precursors such as orthosilicic esters, alkoxysilanes, alkoxytitanates, alkoxyaluminates can also be used. Specific examples are tetramethoxysilane, tetraethoxysilane, tetrapropoxysilane, tetrabutoxysilane, and analogous tetraalkoxytitanium, and trialkoxyaluminium compounds. Precursors are converted to the corresponding binder during mixing, spray drying, or calcination.

The catalyst comprises a noble metal. Suitable noble metals include gold, silver, platinum, palladium, iridium, ruthenium, osmium, rhenium, rhodium, and mixtures thereof. Preferred noble metals are Pd, Pt, Au, Re, Ag, and mixtures thereof. Palladium, gold, and their mixtures are particularly desirable. Typically, the amount of noble metal present in the catalyst will be in the range of from 0.01 to 20 wt. %, preferably 0.1 to 5 wt. %.

There are no particular restrictions regarding the choice of the noble metal compound or complex used as the source of the noble metal. Suitable compounds include nitrates, sulfates, halides (e.g., chlorides, bromides), carboxylates (e.g., acetate), and amine or phosphine complexes of noble metals (e.g., palladium(II) tetraammine bromide, tetrakis(triphenylphosphine) palladium(0)).

The weight ratio of the transition metal zeolite to noble metal is not particularly critical. However, a transition metal zeolite to noble metal weight ratio of from 100:1 to 10,000:1 (grams of transition metal zeolite per gram of noble metal) is preferred.

The noble metal may be supported on a carrier. Suitable carriers include silica, alumina, titania, silica-alumina, silica-titania, clays, carbons, ion-exchange resins, and the like. Titania is a preferred carrier.

The oxidation state of the noble metal in the catalyst is not critical. Palladium, for instance, may be in an oxidation state anywhere from 0 to +4 or any combination of such oxidation states. To achieve the desired oxidation state or combination of oxidation states, the noble metal compound after being introduced in the catalyst may be fully or partially pre-reduced.

The catalyst comprises a thiol. A thiol is an organic molecule having a general formula RSH and containing a carbon-sulfur single bond, where R contains at least one carbon atom. R may be an alkyl or aryl group. The term "thiol" also includes thiolate, $RS^-$. R may contain substituents such as hydroxy, ketone, ester, amide, halide, cyano, nitro, amino, carboxylic acid or carboxylate, and the like. Thiols are also called mercaptans. Suitable thiols include methanethiol, ethanethiol, 1-propanethiol, 2-propanethiol, 1-butanethiol, 2-butanethiol, 2-methyl-1-propanethiol, 2-methyl-2-propanethiol, 1-dodecanethiol, cyclohexanethiol, benzenethiol (thiophenol), alpha-toluenethiol (benzyl mercaptan), alkyl mercaptopropionates, 3-mercaptopropionic acid, 2-mercaptoethanol, 1,2-ethanedithiol, and mercaptoacetic acid. An organic polymer carrying —SH groups may be also used. Preferably, the —SH group of the thiol is bonded to an aliphatic carbon, e.g., in methanethiol, ethanethiol, 1-propanethiol, 2-propanethiol, 1-butanethiol, 2-butanethiol, 2-methyl-1-propanethiol, 2-methyl-2-propanethiol, 1-dodecanethiol, and cyclohexanethiol. A thiolate salt (e.g., ammonium, sodium, or potassium salt) may be use as the source of the thiol.

The thiols may be present in the catalyst as free molecules. Alternatively, the thiol may be tethered to the transition metal zeolite through a chemical linkage (i.e., covalent chemical bonds) so that the transition metal zeolite is functionalized with thiol groups. Zeolite surfaces contain hydroxy groups. Any suitable chemical linkage may be used to tether a thiol to zeolite surfaces. For example, a hydroxy- or halide-substituted thiol (e.g., 2-mercaptoethyl chloride, 3-mercaptopropyl bromide) may react with a zeolite surface hydroxy group to form an ether linkage. A thiol containing a carboxylic acid or a carboxylic halide group (e.g., 2-mercaptoacetic chloride, 3-mercaptopropionic bromide) may be used to functionalize a zeolite through ester functionalities. Trialkoxysilyl-substituted thiols (e.g., 3-mercaptopropyl trimethoxysilane, 2-mercaptoethyl trimethoxysilane) are particularly preferred functionalizing agents. It is known that a thiol group can be tethered to a mesoporous silica by reacting it with 3-mercaptopropyl trimethoxysilane. See *Ind. Eng., Chem. Res.* 43 (2004) 1478.

If the catalyst includes a binder, the thiol may be tethered to the binder. For example, a spray-dried transition metal zeolite containing a silica binder may be treated with 3-mercaptopropyl trimethoxysilane to give a material in which the silica binder and/or the transition metal zeolite are functionalized by thiol groups. Other binders may be functionalized in a similar fashion.

Similarly, if the noble metal is supported on a carrier, the thiol may be tethered to the carrier in a similar manner. It is known that silicas, aluminas, titanias, carbons, and the like, contain surface hydroxy group that may react with a functionalizing agent, such as 3-mercaptopropyl trimethoxysilane.

It is presumed that the thiol modifies the chemical activities of the noble metal so that it improves the catalyst selectivity in chemical reactions, e.g., the epoxidation of olefin with hydrogen and oxygen. Preferably, the thiol and the noble metal are in close proximity to favor the interaction between them. In one preferred catalyst, the noble metal is supported on a transition metal zeolite particle while the thiol is grafted on the same particle. In another preferred catalyst, the noble metal is supported on a carrier while the thiol is grafted on the same carrier.

The amount of thiol in the catalyst is not critical. Generally, the molar ratio of thiol to the noble metal is in the range of from 1:9 to 9:1. Preferably the ratio is in the range of from 3:1 to 1:3.

In another aspect, the invention is an epoxidation process comprising reacting an olefin, oxygen, and hydrogen in a presence of the catalyst of the invention.

An olefin is used in the process. Suitable olefins include any olefin having at least one carbon-carbon double bond, and generally from 2 to 60 carbon atoms. Preferably the olefin is an acyclic alkene of from 2 to 30 carbon atoms; the process is particularly suitable for epoxidizing $C_2$-$C_6$ olefins. More than one double bond may be present in the olefin molecule, as in a diene or triene. The olefin may be a hydrocarbon or may contain functional groups such as halogen, carboxyl, hydroxyl, ether, carbonyl, cyano, or nitro groups, or the like. In a particularly preferred process, the olefin is propylene and the epoxide is propylene oxide.

Oxygen and hydrogen are required. Although any sources of oxygen and hydrogen are suitable, molecular oxygen and molecular hydrogen are preferred. The molar ratio of hydrogen to oxygen can usually be varied in the range of $H_2:O_2$=1:100 to 5:1 and is especially favorable at 1:5 to 2:1. The molar ratio of oxygen to olefin is usually 1:1 to 1:20, and preferably 1:1.5 to 1:10. Relatively high oxygen to olefin molar ratios (e.g., 1:1 to 1:3) may be advantageous for certain olefins.

In addition to the olefin, oxygen, and hydrogen, an inert gas is preferably used in the process. Any desired inert gas can be used. Suitable inert gases include nitrogen, helium, argon, and carbon dioxide. Saturated hydrocarbons with 1-8, especially 1-6, and preferably 1-4 carbon atoms, e.g., methane, ethane, propane, and n-butane, are also suitable. Nitrogen and saturated $C_1$-$C_4$ hydrocarbons are preferred inert gases. Mixtures of inert gases can also be used. The molar ratio of olefin to gas is usually in the range of 100:1 to 1:10 and especially 20:1 to 1:10.

The process may be performed in a continuous flow, semi-batch, or batch mode. A continuous flow process is preferred. The catalyst is preferably in a slurry.

It is advantageous to work at a pressure of 1-200 bars. The process is carried out at a temperature effective to achieve the desired olefin epoxidation, preferably at temperatures in the range of 0-200° C., more preferably, 20-150° C. Preferably, at least a portion of the reaction mixture is a liquid under the reaction conditions.

A reaction solvent is preferably used in the process. Suitable reaction solvents are liquid under the reaction conditions. They include, for example, oxygen-containing hydrocarbons such as alcohols, aromatic and aliphatic solvents such as toluene and hexane, nitrites such as acetonitrile, carbon dioxide, and water. Suitable oxygenated solvents include alcohols, ethers, esters, ketones, carbon dioxide, water, and the like, and mixtures thereof. Preferred oxygenated solvents include water and lower aliphatic $C_1$-$C_4$ alcohols such as methanol, ethanol, isopropanol, tert-butanol, and mixtures thereof. Fluorinated alcohols can be used.

Where a reaction solvent is used, it may be advantageous to use a buffer. The buffer is employed in the reaction to inhibit the formation of glycols or glycol ethers during the epoxidation, and it can improve the reaction rate and selectivities. The buffer is typically added to the solvent to form a buffer solution, or the solvent and the buffer are added separately. Useful buffers include any suitable salts of oxyacids, the nature and proportions of which in the mixture are such that the pH of their solutions preferably ranges from 3 to 12, more preferably from 4 to 10, and most preferably from 5 to 9. Suitable salts of oxyacids contain an anion and a cation. The anion may include phosphate, carbonate, bicarbonate, sulfate, carboxylates (e.g., acetate), borate, hydroxide, silicate, aluminosilicate, or the like. The cation may include ammonium, alkylammonium (e.g., tetraalkylammoniums, pyridiniums), alkylphosphonium, alkali metal, and alkaline earth metal ions, or the like. Examples include $NH_4$, $NBu_4$, $NMe_4$, Li, Na, K, Cs, Mg, and Ca cations. The preferred buffer comprises an anion selected from the group consisting of phosphate, carbonate, bicarbonate, sulfate, hydroxide, and acetate; and a cation selected from the group consisting of ammonium, alkylammonium, alkylphosphonium, alkali metal, and alkaline earth metal ions. Buffers may preferably contain a combination of more than one suitable salt. Typically, the concentration of the buffer in the solvent is from 0.0001 M to 1 M, preferably from 0.0005 M to 0.3 M. The buffer may include ammonium hydroxide which can be formed by adding ammonia gas to the reaction system. For instance, one may use a pH=12-14 solution of ammonium hydroxide to balance the pH of the reaction system. More preferred buffers include alkali metal phosphates, ammonium phosphate, and ammonium hydroxide. The ammonium phosphate buffer is particularly preferred.

Following examples illustrate the invention.

EXAMPLE 1

Spray-Dried TS-1

CATALYST A

Titanium silicalite-1 (TS-1) is prepared by following procedures disclosed in U.S. Pat. Nos. 4,410,501 and 4,833,260, and calcined in air at 550° C. Spray-dried TS-1 is prepared by following procedures disclosed in U.S. Pat. Appl. Pub. No. 20070027347. It is calcined in air at 550° C. The calcined spray-dried TS-1 (Catalyst A) contains approximately 80 wt. % TS-1 and 20 wt. % silica.

EXAMPLE 2

Pd/Au/Titania

Catalyst B

An aqueous slurry containing 17.5 wt. % titania is prepared with $TiO_2$ (Millennium Inorganic Chemicals S5-300B). The slurry is dried with a Mobile Minor Spray Dryer (Niro Inc.) configured for a two-point powder discharge and a rotary atomizer. The Drying Chamber has an inside diameter of 2.7 feet and a 2-feet cylindrical height with a 60-degree angle conical bottom. A Watson Marlow peristaltic pump (model 521CC) is use to feed the slurry to the atomizer wheel and control the exit temperature. The main product is collected at the bottom port of the drying chamber and fines are routed to the cyclone collector. Air is used as drying/process gas at a flow rate of 80 kg/h. The inlet temperature is set at 220° C. The atomizer wheel is set to 27,000 RPM. A Watson Marlow peristaltic pump is used to evaporate de-ionized water and control the exit temperature of the drying chamber to 95° C. The product is collected at the bottom of the drying chamber. Its mean mass diameter is 24 μm. The spray-dried titania is calcined in air at 700° C. The calcined spray-dried titania has a surface area of 40 $m^2/g$.

A round-bottom flask is charged with 25 mL of deionized water. To the water, 0.265 g of aqueous sodium tetrachloro aurate (20.74 wt. % gold), 0.275 g of disodium palladium tetrachloride, and 10 g of calcined spray-dried titania prepared above is added. To this slurry, 0.26 g of solid sodium bicarbonate is added. The slurry is agitated by rotating the flask at 25 rpm at a 45-degree angle for 4 h at 40° C. and filtered. The solids are washed once with 25 mL of deionized water. The solids are then calcined in air by heating at 10° C./min to 110° C. and holding at 110° C. for 4 h, then heating at 2° C./min to 300° C. and holding at 300° C. for 4 h. The calcined solids are washed with deionized water (25 mL×8). The solids are calcined in air by heating at 10° C./min to 110° C. for 4 h and then at 2° C./min to 550° C. for 4 h. The solids are then transferred to a quartz tube and treated with a hydrogen/nitrogen (mole ratio 4:96, 100 mL/h) gas at 100° C. for 1 h, followed by nitrogen for 30 min as the catalyst cooled from 100° C. to 30° C. The solids obtained (Catalyst B) contain 0.95 wt. % palladium, 0.6 wt. % gold, 58 wt. % titanium, and less than 20 ppm chloride.

EXAMPLE 3

Thiol-Functionalized Pd/Au/Titania

Catalyst C

Catalyst B (20 g), 3-mercaptopropyl trimethoxysilane (3 g), toluene (85 g) are added to a 450-mL Parr reactor. The reactor is sealed and heated to 120° C. for 4 h under helium. The solid is isolated by filtration, washed with toluene (50 mL), then with acetone (50 mL), and finally with ethanol (50 mL). It is dried under vacuum at 60° C. for 4 h. The solids are then transferred to a 450-mL Parr reactor and treated with a mixture of hydrogen (120 psig) and nitrogen (400 psig) at 60° C. for 2 h. The resulting material (Catalyst C) contains 1.1 wt. % of S, 0.91 wt. % Pd, and 0.58 wt. % Au.

EXAMPLE 4

Thiol-Functionalized Spray-Dried TS-1

Catalyst D

Spray-dried TS-1 (27 g), 3-mercaptopropyl trimethoxysilane (4.1 g), and toluene (100 g) are added to a 450-mL Parr reactor. The reactor is sealed and heated to 120° C. for 4 h under helium atmosphere. The solid is isolated by filtration, washed with toluene, then with acetone, and finally with ethanol. It is dried under vacuum at 60° C. for 4 h. The resulting material (Catalyst D) contains 0.93 wt. % of S.

EXAMPLE 5

Thiol-Functionalized Pd/TS-1

Catalyst E

A mixture containing palladium acetate (0.128 g), toluene (50 g), and Catalyst D (12 g) is mixed under nitrogen atmosphere for 30 min at room temperature. The solid is isolated by filtration, washed with toluene (40 mL×2) and ethanol (40 mL×2). The solid is dried under vacuum at 60° C. The solids are then transferred to a 450-mL Parr reactor and treated with a mixture of hydrogen (120 psig) and nitrogen (400 psig) at 60° C. for 2 h. The solids obtained (Catalyst E) contains 1.0 wt. % S and 0.47 wt. % Pd.

EXAMPLE 6

Thiol-Functionalized Pd/TS-1

Catalyst F

A mixture containing palladium acetate (0.39 g), toluene (120 g), and Catalyst D (12 g) is mixed under nitrogen atmosphere for 30 min at room temperature. The solid is isolated by filtration, washed with toluene (40 mL×2) and ethanol (40 mL×2). The solid is dried under vacuum at 60° C. The solids are then transferred to a 450-mL Parr reactor and treated with a mixture of hydrogen (120 psig) and nitrogen (400 psig) at 60° C. for 2 h. The solids obtained (Catalyst F) contains 1.0 wt. % S and 1.2 wt. % Pd.

EXAMPLE 7

Thiol-Functionalized Pd/Au/Titania

Catalyst G

A sample of spray-dried titania from Example 2 (31 g), 3-mercaptopropyl trimethoxysilane (4 g), and toluene (120 g) are added to a 450-mL Parr reactor. The reactor is sealed and heated to 120° C. for 4 h under helium. The solid is isolated by filtration, washed with toluene, then washed with acetone, and ethanol respectively. It is dried under vacuum at 60° C. for 4 h. The resulting material (thiol-functionalized titania) contains 0.84 wt. % of S.

A solution containing palladium acetate (0.23 g) and toluene (85 g) is added to a sample of thiol-functionalized titania prepared above (10 g) under nitrogen atmosphere. It is mixed for 30 min at room temperature. The solid is isolated by filtration, washed twice with toluene and twice with ethanol. The solid is dried under vacuum at 60° C. The solids are then transferred to a 450-mL Parr reactor and treated with a mixture of hydrogen (120 psig) and nitrogen (400 psig) at 60° C. for 2 h. The solids obtained (Catalyst G) contains 0.79 wt. % S, 0.93 wt. % Pd.

EXAMPLE 8

Propylene Epoxidation

A 450-mL Parr reactor is charged with Catalyst B (1.2 g), Catalyst D (5.1 g), and 220 g methanol/water (80/20 in weight) solution containing 0.01 M ammonium phosphate. The reactor is then charged to 300 psig with a feed gas consisting of 2.8 volume percent (vol. %) hydrogen, 4.5 vol. % oxygen, 4 vol. % propylene, 0.5 vol. % methane, and the balance nitrogen. The pressure in the reactor is maintained at 300 psig. A methanol/water (80/20 in weight) solution containing 0.01 M ammonium phosphate is continuously fed to the reactor at a flow rate of 90 mL/h. The reaction mixture is heated to 60° C. while it is stirred at 1000 rpm. The gaseous effluent is analyzed by an online gas chromatograph (GC). The liquid is analyzed by an offline gas chromatograph (LC). The reaction continues for 40 h. The products formed include propylene oxide (PO), propane, and derivatives of propylene oxide such as propylene glycol, propylene glycol monomethyl ethers, dipropylene glycol, and dipropylene glycol methyl ethers. The calculated results at 40 h are shown in Table 1. The catalyst productivity is defined as the grams of PO formed (including PO which is subsequently reacted to form PO derivatives) per gram of catalyst per hour. POE (mole)=moles of PO+moles of PO units in the PO derivatives. PO/POE selectivity=(moles of PO)/(moles of POE)×100. Propylene to propane selectivity=(moles of propane)/(moles of propane formed+moles of POE)×100.

EXAMPLES 9, 10

Propylene Epoxidation

The procedure of Example 8 is repeated except with different catalysts as shown in Table 1

COMPARATIVE EXAMPLE 11

Pd/TS-1

Catalyst H

Catalyst H is prepared by impregnating Catalyst A using a procedure disclosed in Example 1 of WO 2006/130295. Catalyst H contains 1.5 wt. % Ti and 0.1 wt. % Pd.

COMPARATIVE EXAMPLES 12,13

Propylene Epoxidation

The procedure of Example 8 is repeated except with different catalysts as shown in Table 1.

Results in Table 1 shows that a catalyst containing a transition metal zeolite, a noble metal, and a thiol gives lower selectivity to propane in the epoxidation of propylene by hydrogen and oxygen (Examples 8, 9, 10) than those that do not contain a thiol (Examples 12 and 13). The POE productivities are similar among all these reactions. In addition, the molar ratios of hydrogen/oxygen consumed in Examples 8-10 are generally lower than those in Examples 12 and 13. The reaction between hydrogen and oxygen to form water consumes hydrogen and oxygen in a molar ratio of 2/1. On the other hand, the reaction of propylene, hydrogen, and oxygen to form propylene oxide and water consumes hydrogen and oxygen in a molar ratio of 1/1. Thus a lower molar ratio of hydrogen to oxygen consumed indicates that the catalyst is more selective to epoxide.

In Example 8, Catalyst D is functionalized by thiol groups, and Catalyst B is not. The mixture of Catalysts B and D gives 4% propane selectivity, which is lower than that in Example 13. The results indicate that the thiol groups of Catalyst D modifies the hydrogenation activity of Catalyst B, so that the catalyst mixture is more selective to epoxide.

A catalyst comprising a thiol grafted on the solid components of the catalyst (zeolite, carrier, or binder) has an additional advantage: the thiol is tethered to the solid, so the catalyst may be easily recycled and reused. It is particularly useful in a continuous reaction as the solid catalyst and the tethered thiol remain in the reactor as the liquid (or gas) reaction mixture continuously exits the reactor.

TABLE 1

Epoxidation of Propylene

| Ex. | Catalyst | Feed $H_2/O_2$ (mol/mol) | Consumed $H_2/O_2$ (mol/mol) | Propane Selectivity (%) | PO/POE Selectivity (%) | POE Productivity (g POE/g/h) |
|---|---|---|---|---|---|---|
| 8 | Catalyst E (Thiol-functionalized Pd/TS-1): 5.1 g<br>Catalyst B (Pd/Au/titania): 1.2 g | 0.63 | 1.89 | 4.0 | 91 | 0.26 |
| 9 | Catalyst A (Spray-dried TS-1): 5.4 g<br>Catalyst G (Thiol-functionalized Pd/titania): 0.6 g | 0.83 | 1.37 | 5.0 | 88 | 0.29 |
| 10 | Catalyst F (Thiol-functionalized Pd/TS-1): 6.0 g | 0.50 | 1.08 | 2.0 | 91 | 0.28 |
| C. 12 | Catalyst H (Pd/TS-1): 6.0 g | 0.66 | 1.83 | 11 | 89 | 0.33 |
| C. 13 | Catalyst A (Spray-dried TS-1): 4.8 g<br>Catalyst B (Pd/Au/titania): 1.2 g | 0.66 | 2.16 | 11 | 91 | 0.29 |

I claim:

1. A catalyst comprising a transition metal zeolite, palladium, and a thiol, wherein the thiol is tethered to the transition metal zeolite.

2. The catalyst of claim 1 wherein the transition metal zeolite is a titanium zeolite.

3. The catalyst of claim 1 wherein the transition metal zeolite is TS-1.

4. The catalyst of claim 1 further comprising gold.

5. A catalyst comprising a transition metal zeolite, palladium, a thiol, and a binder, wherein the thiol is tethered to the binder.

6. An epoxidatibn process comprising reacting an olefin, hydrogen, and oxygen in the presence of a catalyst comprising a transition metal zeolite, palladium, and a thiol.

7. The process of claim 6 wherein the transition metal zeolite is a titanium zeolite.

8. The process of claim 6 wherein the transition metal zeolite is TS-1.

9. The process of claim 6 wherein the catalyst further comprises gold.

10. The process of claim 6 performed in the presence of a solvent.

11. The process of claim 10 wherein the solvent is an oxygenated solvent.

12. The process of claim 11 wherein the solvent is selected from the group consisting of water, methanol, ethanol, isopropanol, tert-butanol, and mixtures thereof.

13. The process of claim 6 performed in the presence of a buffer.

14. The process of claim 13 wherein the buffer is an ammonium phosphate.

15. The process of claim 6 wherein the olefin is propylene.

* * * * *